United States Patent
Selvaraj et al.

(10) Patent No.: US 9,545,227 B2
(45) Date of Patent: Jan. 17, 2017

(54) SLEEP APNEA SYNDROME (SAS) SCREENING USING WEARABLE DEVICES

(71) Applicant: Vital Connect, Inc., Campbell, CA (US)

(72) Inventors: Nandakumar Selvaraj, Santa Clara, CA (US); Ravi Narasimhan, Sunnyvale, CA (US)

(73) Assignee: VITAL CONNECT, INC., Campbell, CA (US)

( * ) Notice: Subject to any disclaimer, the term of this patent is extended or adjusted under 35 U.S.C. 154(b) by 222 days.

(21) Appl. No.: 14/231,547

(22) Filed: Mar. 31, 2014

(65) Prior Publication Data

US 2015/0164410 A1 Jun. 18, 2015

Related U.S. Application Data

(60) Provisional application No. 61/916,024, filed on Dec. 13, 2013.

(51) Int. Cl.
| | | |
|---|---|---|
| A61B 5/00 | (2006.01) | |
| A61B 5/0205 | (2006.01) | |
| A61B 5/04 | (2006.01) | |
| A61B 5/0402 | (2006.01) | |
| A61B 5/0456 | (2006.01) | |
| A61B 5/0452 | (2006.01) | |
| A61B 5/11 | (2006.01) | |

(52) U.S. Cl.
CPC .......... *A61B 5/4818* (2013.01); *A61B 5/0004* (2013.01); *A61B 5/0006* (2013.01); *A61B 5/0205* (2013.01); *A61B 5/0402* (2013.01); *A61B 5/04012* (2013.01); *A61B 5/0456* (2013.01); *A61B 5/11* (2013.01); *A61B 5/1121* (2013.01); *A61B 5/6801* (2013.01); *A61B 5/6833* (2013.01); *A61B 5/7267* (2013.01); *A61B 5/0452* (2013.01); *A61B 5/1116* (2013.01); *A61B 5/7203* (2013.01)

(58) Field of Classification Search
CPC .................................................. A61B 5/4818
USPC ........................................................ 600/301
See application file for complete search history.

(56) References Cited

U.S. PATENT DOCUMENTS

| | | |
|---|---|---|
| 4,589,420 A | 5/1986 | Adams et al. |
| 7,634,360 B2 | 12/2009 | Davalos et al. |

(Continued)

OTHER PUBLICATIONS de Chazal et al. Automated detection of obstructive sleep apnoea at different time scales using the electrocardiogram. Physiological Measurement, vol. 25, 2004, pp. 967-983.

(Continued)

*Primary Examiner* — Amanda Patton
*Assistant Examiner* — Philip C Edwards
(74) *Attorney, Agent, or Firm* — Brundidge & Stanger, P.C.

(57) ABSTRACT

A method and system for Sleep Apnea Syndrome (SAS) screening are disclosed. The method comprises detecting at least one physiological signal, converting the at least one physiological signal into at least one sensor stream, and processing the at least one sensor stream to perform the SAS screening. The system includes a sensor to detect at least one physiological signal, a processor coupled to the sensor, and a memory device coupled to the processor, wherein the memory device includes an application that, when executed by the processor, causes the processor to convert the at least one physiological signal into at least one sensor stream and to processor the at least one sensor stream to perform the SAS screening.

16 Claims, 6 Drawing Sheets

(56) References Cited

U.S. PATENT DOCUMENTS

| | | |
|---|---|---|
| 2007/0208269 A1 | 9/2007 | Mumford et al. |
| 2008/0051669 A1* | 2/2008 | Meyer ................ A61B 5/02405 |
| | | 600/484 |
| 2011/0172501 A1 | 7/2011 | Antonijevic et al. |
| 2011/0251985 A1 | 10/2011 | Waxman et al. |
| 2013/0021158 A1 | 1/2013 | Lyons et al. |
| 2013/0204100 A1 | 8/2013 | Acquista |

OTHER PUBLICATIONS

The International Search Report and the Written Opinion of the International Searching Authority for international application No. PCT/US2014/069983, mailed on May 14, 2015.

The International Search Report and the Written Opinion of the International Searching Authority for international application No. PCT/US2014/069995, mailed on May 14, 2015.

Nandakumar Selvaraj and Ravi Narasimhan, "Automated Prediction of the Apnea-Hypopnea Index using a Wireless Patch Sensor," pp. 1897-1900, 36th Annual International Conference of the IEEE EMBS, Chicago, Illinois USA, Aug. 26-30, 2014.

* cited by examiner

SLEEP APNEA SYNDROME (SAS) SCREENING USING WEARABLE DEVICES

CROSS-REFERENCE TO RELATED APPLICATION

This application claims benefit under 35 USC 119(e) of U.S. Provisional Patent Application No. 61/916,024, filed on Dec. 13, 2013, entitled "SLEEP APNEA SCREENING AND AUTOMATED PREDICTION OF APNEA-HYPOPNEA INDEX USING A WEARABLE PATCH SENSOR," which is incorporated herein by reference in its entirety.

FIELD OF THE INVENTION

The present invention relates to wearable devices, and more particularly, to screening for Sleep Apnea Syndrome (SAS) using wearable devices.

BACKGROUND

The accurate measurement of sleep related diseases such as sleep apnea is important to managing the overall health of a person. Sleep Apnea Syndrome (SAS) is a major sleep disorder that causes recurrent episodes of complete (apnea) or partial (hypopnea) blockage of the upper airway during sleep. One of the metrics that quantify the severity of SAS is the Apnea-Hypopnea Index (AHI) index, which is the number of apnea and hypopnea events per hour averaged over the duration of sleep.

The prevalence of SAS is approximately 3 to 7% in adult men and 2 to 5% in adult women and the disease prevalence in higher in different population subsets such as the obese or older groups. Additionally, there is a large proportion of undiagnosed SAS patients because routine clinical visits and blood tests usually do not detect SAS. Accurate SAS screening is important because there are adverse health consequences of this disorder, including daytime hypersomnolence, neurocognitive dysfunction, cardiovascular disease, metabolic dysfunction and respiratory failure.

Conventional SAS screening is done via an analysis of symptoms (airway, physical) and via cumbersome clinical studies and in-center testing facilities such as the commonly used polysomnography (PSG) test. The PSG test conducted at a sleep center facility requires an abundance of sensors and interferes with the person's normal sleep rhythms. The PSG test also involves high operating costs, in part because of the dedicated equipment, facilities, and personnel required to conduct the test. Additionally, the PSG test is time consuming and often varies based on the subjective interpretation of medical experts.

Therefore, there is a strong need for a solution that overcomes the aforementioned issues. The present invention addresses such a need.

SUMMARY OF THE INVENTION

A method and system for Sleep Apnea Syndrome (SAS) screening are disclosed. The method comprises detecting at least one physiological signal, converting the at least one physiological signal into at least one sensor stream, and processing the at least one sensor stream to perform the SAS screening.

The system includes a sensor to detect at least one physiological signal, a processor coupled to the sensor, and a memory device coupled to the processor, wherein the memory device includes an application that, when executed by the processor, causes the processor to convert the at least one physiological signal into at least one sensor stream and to processor the at least one sensor stream to perform the SAS screening.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

The present invention relates to wearable devices, and more particularly, to screening for Sleep Apnea Syndrome (SAS) using wearable devices. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Sleep Apnea Syndrome (SAS) can be screened using a variety of modalities including but not limited to screening via symptoms (airway, physical), questionnaires, overnight polysomnography (PSG) tests that analyze the Apnea-Hypopnea Index (AHI) (manual event-by-event analysis of airflow and oxygen saturation SpO2 signals to quantify the severity of the SAS), home sleep tests, and portable SAS monitor devices.

The portable SAS monitor devices (e.g. Type-4 monitors) include but are not limited to respiratory and effort sensors that utilize at least one channel (e.g. oxygen saturation or airflow). The limitations of the existing portable monitors include complex sensor attachment, obtrusiveness, detachment of sensors and compliance issues.

A method and system in accordance with the present invention provides a wireless, portable, and wearable sensor device ("wearable device") that is in a patch form factor and that is attached to a user to automatically and continuously detect a plurality of health related and physiological signals including but not limited to ECG and acceleration signals. The wearable device utilizes an embedded electronic module and a plurality of algorithms to process the detected physiological signals and convert them into a plurality of sensor streams.

In the method and system, the plurality of sensor streams are additionally processed either by the internal processor of the wireless device or by an external processor/device including but not limited to a sensor/relay/cloud processor and a smartphone device. After the additional processing that comprises any of preprocessing, feature extraction, and machine learning optimization, the method and system automatically predict whether the user may have SAS disorder. The method and system output various indications on a display including but not limited to identifications of whether the user has or is at risk for SAS.

In one embodiment, a wearable device is used to accurately detect a variety of health related concerns including sleep related diseases such as SAS. The wearable device utilizes a plurality of sensors and integrated algorithms to automatically screen the subjects to determine whether they may have the risks of SAS disorder using overnight/multi-night assessment. The accurate screening of SAS is achieved out-of-center and in a more comfortable setting for the patient.

Figure 1:
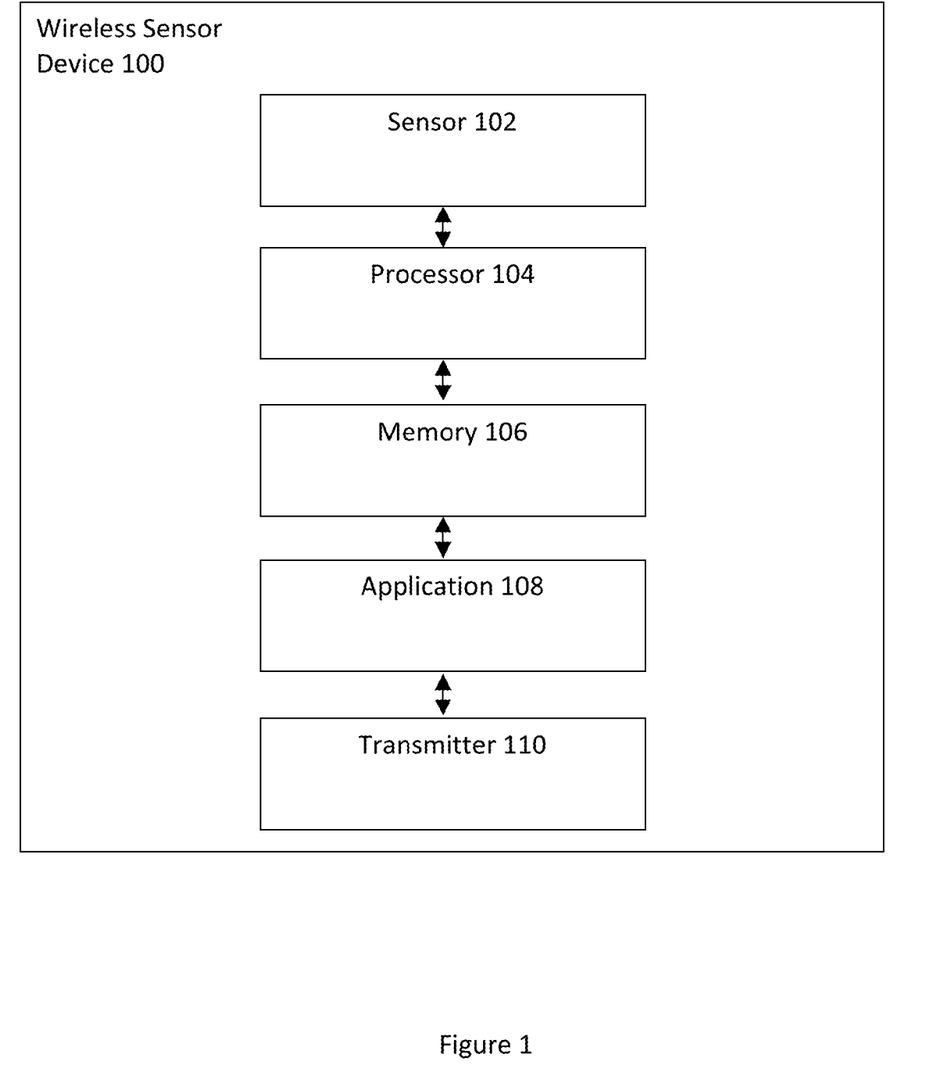
FIG. 1 illustrates a wireless sensor device for Sleep Apnea Syndrome (SAS) screening in accordance with an embodiment.

FIG. 1 illustrates a wireless sensor device 100 for Sleep Apnea Syndrome (SAS) screening in accordance with an embodiment. The wireless sensor device 100 or wearable device includes a sensor 102, a processor 104 coupled to the sensor 102, a memory 106 coupled to the processor 104, an application 108 coupled to the memory 106, and a transmitter 110 coupled to the application 108.

In one embodiment, the wireless sensor device 100 is attached to a user to detect various physiological signals via the sensor 102. The sensor 102 obtains data from the user, which is transmitted to the memory 106 and in turn to the application 108 via the processor 104. The processor 104 executes the application 108 to process and obtain information regarding the user's health. The information is transmitted to the transmitter 110 and in turn relayed to another user or device for further processing, analysis, and storage. In another embodiment, the transmitter 110 transmits the various detected physiological signals in raw form to a remote device/server (e.g. smartphone, cloud-based server) for processing, analysis, and storage.

In one embodiment, the sensor 102 is any of a microelectromechanical system (MEMS) tri-axial accelerometer and an embedded sensor with electrodes and the processor 104 is a microprocessor. One of ordinary skill in the art readily recognizes that a variety of devices can be utilized for the sensor 102, the processor 104, the memory 106, the application 108, and the transmitter 110 and that would be within the spirit and scope of the present invention.

Additionally, one of ordinary skill in the art readily recognizes that a variety of wireless sensor devices can be utilized including but not limited to wearable devices, a wireless sensor device in a patch form-factor, the Vital Connect HealthPatch™ wearable device, electrocardiograph devices, tri-axial accelerometers, uni-axial accelerometers, bi-axial accelerometers, gyroscopes, and pressure sensors and that would be within the spirit and scope of the present invention.

To describe the features of the present invention in more detail, refer now to the following description in conjunction with the accompanying Figures.

Figure 2:
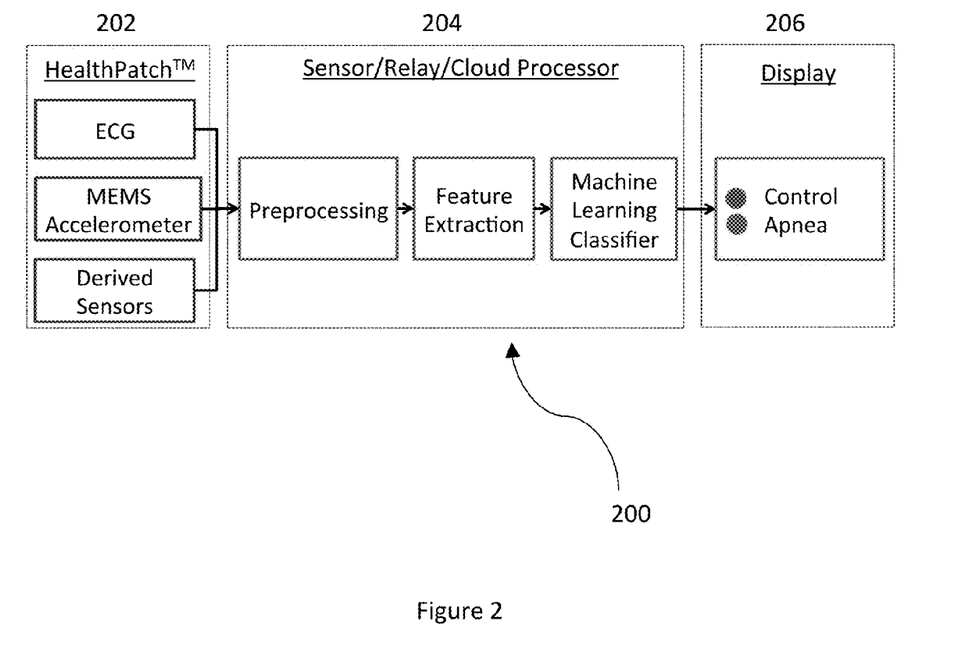
FIG. 2 illustrates a flow chart of a system for Sleep Apnea Syndrome (SAS) screening in accordance with an embodiment.

FIG. 2 illustrates a flow chart of a system 200 for Sleep Apnea Syndrome (SAS) screening in accordance with an embodiment. The system 200 includes a wearable device 202 and a relay/cloud processor 204 that is coupled to both the wearable device 202 and to a display unit 206. In another embodiment, the processing capabilities of the relay/cloud processor 204 are embedded within the wearable device 202.

In FIG. 2, the wearable device 202 includes a plurality of sensors including but not limited to an electrocardiograph (ECG) sensor, a tri-axial MEMS accelerometer, and other derived sensors. The relay/cloud processor 204 includes a plurality of processing capabilities including but not limited to preprocessing, feature extraction, and machine learning classifier optimization. The display unit 206 displays a plurality of outputs including but not limited to the prediction of whether the user belongs to a control category versus an apnea category, or belongs to a control-to-mild apnea group versus a moderate-to-severe apnea group.

In one embodiment, the SAS screening is accomplished using a system that comprises a wearable device with embedded sensors that automatically and continuously detects and records physiological data signals of a patient/user for a predetermined time period (e.g. overnight, multi-night) and processes the physiological data signals into data streams. In another embodiment, demographic information of the patient/user and responses to a plurality of sleep related questionnaires are also utilized by the system in combination with the data streams for the SAS screening. The demographic information includes but is not limited to height, weight, age, neck circumference, body mass index, and gender. The sleep related questionnaires include but are not limited to STOP_BANG questionnaire, Epworth Sleepiness scale and Berlin questionnaire.

In this embodiment, the system utilizes SAS screening algorithms located on any of the wearable device and an external system in communication (e.g. via WiFi, Bluetooth, etc.) with the wearable device to analyze and process the data streams that have been determined by the wearable device. In one embodiment, the external system is any of a relay/cloud processor, a smartphone device, a cloud computing system and database, and a cloud-based server. In another embodiment, the SAS screening algorithms are embedded into the wearable device that processes the data streams processed from physiological signals that have been detected and recorded.

The SAS screening algorithms produce outputs at a display unit and the outputs include but are not limited to a green light indicator and a red light indicator that correspond to positive and negative results respectively as per group definitions of SAS findings. In one embodiment, the groups are defined as: control (AHI<5) versus apnea subjects (AHI>=5); apnea low-risk e.g., control-to-mild apnea (AHI<15) versus apnea high-risk e.g., moderate-to-severe apnea (AHI>=15) subjects; and control-to-moderate apnea (AHI<30) versus severe apnea (AHI>=30) subjects.

Figure 3:
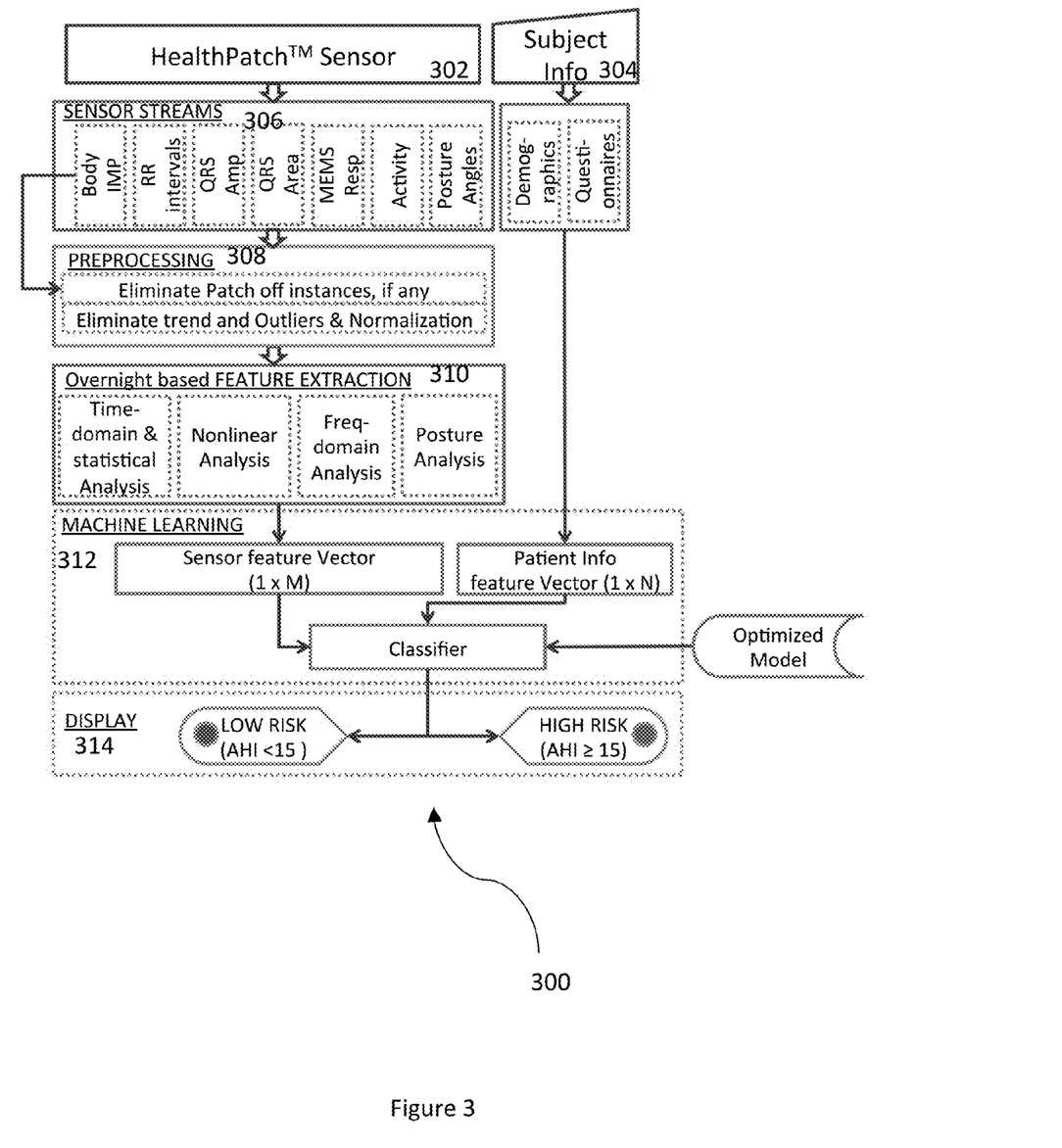
FIG. 3 illustrates a more detailed flow chart of a system for Sleep Apnea Syndrome (SAS) screening in accordance with an embodiment.

FIG. 3 illustrates a more detailed flow chart of a system 300 for Sleep Apnea Syndrome (SAS) screening in accordance with an embodiment. The system 300 includes a wearable device 302, subject information inputs 304, a sensor stream unit 306, a preprocessing unit 308, a feature extraction unit 310, a machine learning unit 312, and a display unit 314. Each of the components (302 to 314) of the system 300 is coupled serially.

In one embodiment, the sensor stream unit 306, the preprocessing unit 308, the feature extraction unit 310, the machine learning unit 312, and the display unit 314 are all embedded within the wearable device 302 and operated together using a sleep apnea screening algorithm. In another embodiment, the aforementioned units 306 to 314 are stand-alone devices that are coupled to and in communication with the wearable device 302 or are all combined to form one external system including but not limited to a relay/cloud processor (e.g. smartphone device).

In one embodiment, the sensor stream unit 306 processes a plurality of physiological data signals that are detected and recorded by the wearable device 302 to derive a plurality of sensor streams including but not limited to body impedance (IMP), RR intervals, QRS amplitudes, QRS areas, MEMS respiratory signals, activity/movement, and posture angles; the subject information inputs 304 include but are not limited to demographic information and sleep questionnaires; the preprocessing unit 308 eliminates instances (if any) of when the wearable device 302 is off, eliminates trends, detects and eliminates outliers, and normalizes the plurality of sensor streams; the feature extraction unit 310 is overnight based and includes but is not limited to time-domain and statistical analysis, nonlinear analysis, frequency-domain analysis, and posture analysis; the machine learning unit 312 provides inputs into a classifier that include any of a sensor feature Vector (1×M), a patient info feature Vector (1×N), and an optimized model; and the display unit 314 includes but is not limited to a low risk (AHI<15) first indicator and a high risk (AHI>=15) second indicator.

In FIG. 3, the wearable device 302 utilizes at least one sensor to detect and record at least one physiological data signal and then utilizes the sensor stream unit 306 to process the at least one physiological data signal to derive sensor streams. The derived sensor streams are transmitted to an internal processing unit of the wearable device 302 or to an external relay/cloud processor unit for further processing.

In one embodiment, the derived sensor streams are transmitted to a relay/cloud processor (e.g. smartphone device, cloud server database) that includes a preprocessing unit 308 for preprocessing. After preprocessing, the preprocessed sensor streams are transmitted to a feature extraction unit 310 of the relay/cloud processor for overnight based feature extraction that determines a feature vector. After feature extraction, the extracted sensor streams and determined feature vector are transmitted to a machine learning unit 312 of the relay/cloud processor for classification of the user using data analytics of learned outputs and optimized machine learning model parameters. The predicted outputs are displayed on the display unit 314 of the relay/cloud processor.

In one embodiment, the wearable device 302 is a HealthPatch™ device. The HealthPatch™ device is an adhesive, wireless patch sensor device that is attached to the chest of a patient/user on predetermined locations and orientations. In one embodiment, the predetermined locations include any of the left midclavicular line over intercostal space (ICS) 2 in a modified lead-II configuration, vertically over the upper sternum, and horizontally on the left midclavicular line over ICS 6. The HealthPatch™ device is utilized to remotely monitor physiological signals of a user/patient including but not limited to ECG and accelerometer signals.

In this embodiment, the HealthPatch™ device's electronic module processes raw physiological data (e.g. raw ECG, and accelerometer signals) and produces a plurality of derived sensor streams. The plurality of derived sensor streams include but are not limited to RR intervals, amplitude of the QRS waveform (RWA), unsigned/signed area of the QRS waveform (RA), MEMS derived respiration signals ($Resp_{MEMS}$), signal magnitude area (SMA) of acceleration signals, and posture angles. In one embodiment, the HealthPatch™ device is wirelessly connected to a relay such as a smartphone device via Bluetooth Low Energy (BLE). The raw physiological data and the derived sensor streams are stored on at least one device including but not limited to the wearable device 302, an external device (e.g. smartphone), and a server for further analysis.

After detection of the raw physiological data by the wearable device 302 and processing of the raw data to derive sensor streams, the derived sensor streams are preprocessed to eliminate noise and artifacts. In one embodiment, the preprocessing unit 308 carries out a plurality of processing steps on the derived sensor streams including but not limited to eliminating wearable device 302 ("patch") off instances, trend removal, and outlier/artifact detection and removal, and normalization. The off instances (if any) are eliminated based on a predefined threshold of body impedance. The predefined threshold is set by any of a third party administrator of the wearable device 302, and another third party such as the manufacturer of the wearable device 302. The preprocessing unit 308 excludes sensor streams from feature extraction during the times when the wearable device 302 is determined to be peeled off or removed from the body.

The preprocessing unit 308 removes trends by applying a moving average filter to generate a very low frequency trend. For example, a moving average filter with a number of beats (e.g. α×user's average Heart Rate (HR), where α is the number of minutes e.g. 3) is applied to the sensor streams to remove trends for ECG derived features such as QRS amplitude and QRS area. Such trend removal is important because changes in postures during sleep such as supine, prone, left and right causes a tremendous shift in the baseline of RWA and RA signals and may introduce potential artifacts and noise in the derived features.

The preprocessing unit 308 detects and removes outliers and artifacts by comparing N and N+1 beats with respect to a predefined threshold. The artifacts/outliers of RWA, RA and $Resp_{MEMS}$ signals are identified as the values outside their respective MN±ββ×SD, where MN refers to the mean value of the respective overnight sensor stream, β is an integer and SD refers to the standard deviation of the respective overnight sensor stream.

The preprocessing unit 308 also normalizes the overnight sensor streams. In one embodiment, the normalization of ECG derived respiration signals is done by applying a filter on the RWA and RA series to compute a moving standard deviation with customized samples to the user (e.g. α×user's average HR). The RWA and RA series are normalized by their respective moving standard deviation values. In another embodiment, the normalization of MEMS derived respiration signals (e.g. $Resp_{MEMS}$) is done by applying a filter on the $Resp_{MEMS}$ signal to compute a moving standard deviation with (α×60×sampling rate of $Resp_{MEMS}$ signal) samples, where α is the number of minutes e.g. 3. The $Resp_{MEMS}$ signal is normalized by its moving standard deviation values.

After the preprocessing, the preprocessed sensor streams are transmitted and fed into the feature extraction unit 310. Features are calculated based on the overnight data analyses of heart rate variability (HRV), ECG and actigraphy derived respiratory signals, posture, and movements. The overnight data analyses consisted of time-domain, frequency-domain, statistical and nonlinear techniques that are applied on the preprocessed overnight sensor streams to obtain the features.

Figure 4:
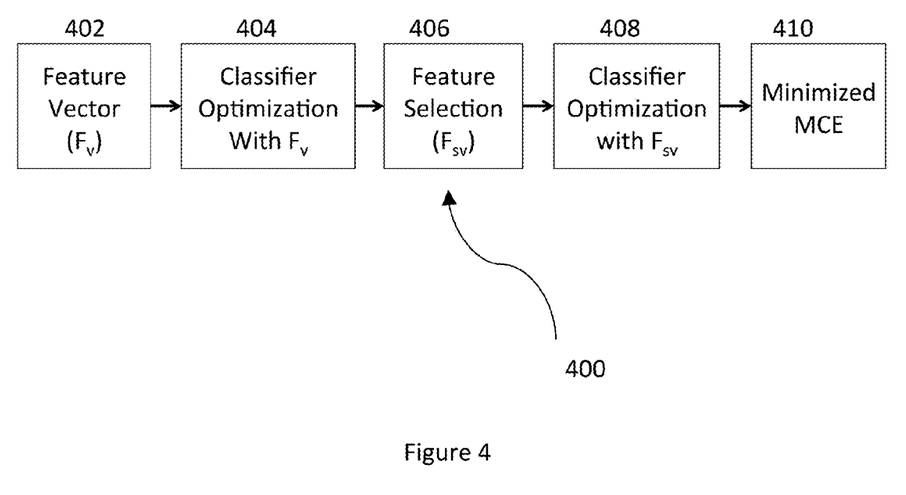
FIG. 4 illustrates a flow chart of an optimization process for SAS classification performed by a machine learning unit.

After the features are extracted from the sensor streams, the sensor features and the user's information features are combined to form the final feature vector ($F_v$). The machine learning unit 312 obtains the classification decision for the user based on the input feature vector $F_v$ and optimized classifier model obtained using an optimization process 400. FIG. 4 illustrates a flow chart of an optimization process 400 for SAS classification performed by a machine learning unit 312. The optimization process 400 receives the feature vector ($F_v$) as an input, via step 402, performs optimization of classifier model parameters using the feature vector ($F_v$), via step 404, performs feature selection using sequential backward selection, via step 406, performs again the optimization of classifier model parameters using the selected/reduced feature vector ($F_{sv}$), via step 408, and outputs a minimum classification error (MCE), via step 410.

Figure 5:
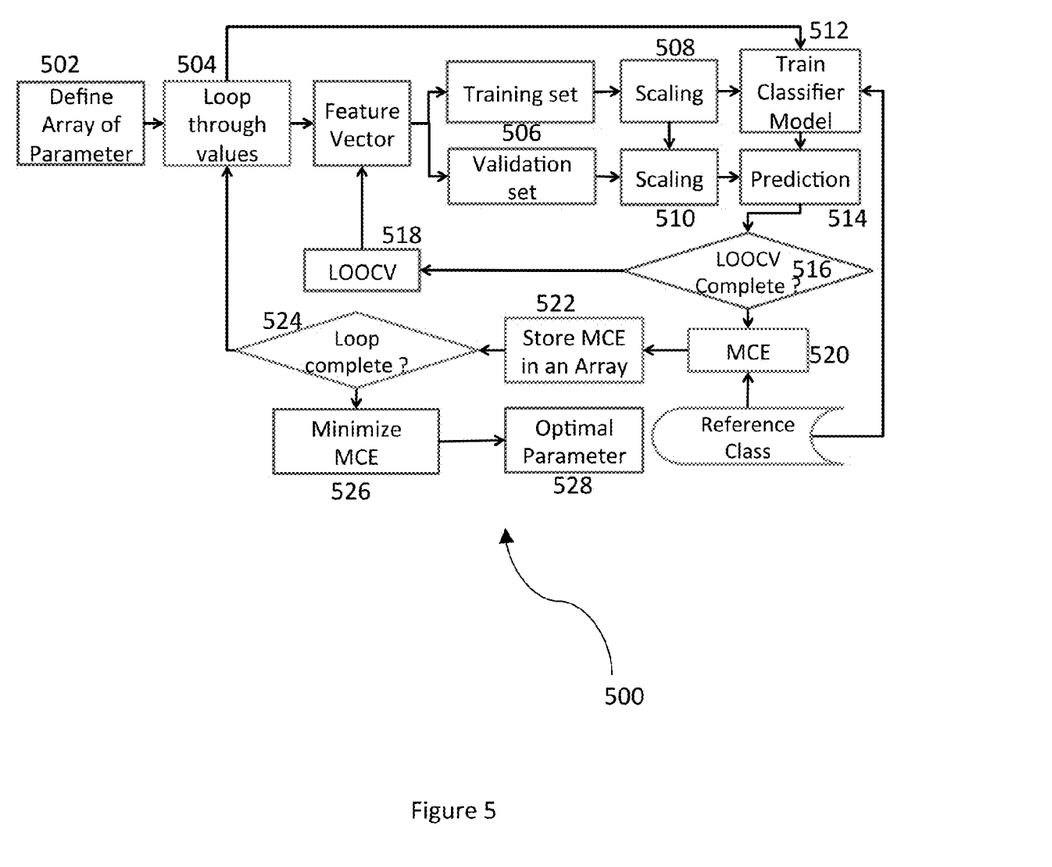
FIG. 5 illustrates a more detailed flow chart of an optimization of classifier model parameters in accordance with an embodiment.

FIG. 5 illustrates a more detailed flow chart of an optimization process 500 of classifier model parameters in accordance with an embodiment. The optimization process 500 provides additional details of the optimization of classifier model parameters performed in steps 404 and 408 of FIG. 4. The optimization process 500 involves leave-one-out cross validation (LOOCV) and generates an optimal classifier model that is used as an input for the machine learning unit 312 in accordance with an embodiment.

The optimization process 500 defines an array of classifier model parameters (e.g. cost function C for linear support vector machines), via step 502, loops through the array of parameters, via step 504, for each value of classifier model parameter the feature matrix is split into a training and a validation data set according to LOOCV, via step 506, performs scaling of the training set, via step 508, performs scaling of the validation set using the shift and scale factors obtained from training set, via step 510, trains a classifier model using the training set, model parameter, and the reference class of the training set, via step 512, determines a prediction using the validation data set and trained classifier model, via step 514, and determines whether (L+1) LOOCV cycles (L refers to the number of training set) are complete, via step 516.

If the L+1 cycles of LOOCV are not complete, the optimization process 500 continues to repeat the steps 506-516 and obtains predictions for (L+1) feature set, via step 518. If the L+1 cycles of LOOCV cycles are complete, the optimization process 500 calculates the misclassification error (MCE) by comparing the predicted class and reference class, via step 520, and stores the computed MCE in an array, via step 522. The optimization process 500 obtains the MCE values for all the other values of model parameters by repeating the steps 504-522 until the looping process 504 is complete, via step 524, determines the least MCE value among the computed MCE values, via step 526, and obtains the optimal model parameter as the one that correspond to the least MCE, via step 528.

The optimization process 500 of the classifier model parameters is carried out at two stages, via steps 404 and 408 of FIG. 4, using complete and reduced feature vector of data sets, respectively. The sequences of the optimization process 400 trains the classifier model to offer the highest performance and least MCE, via step 410.

Figure 6:
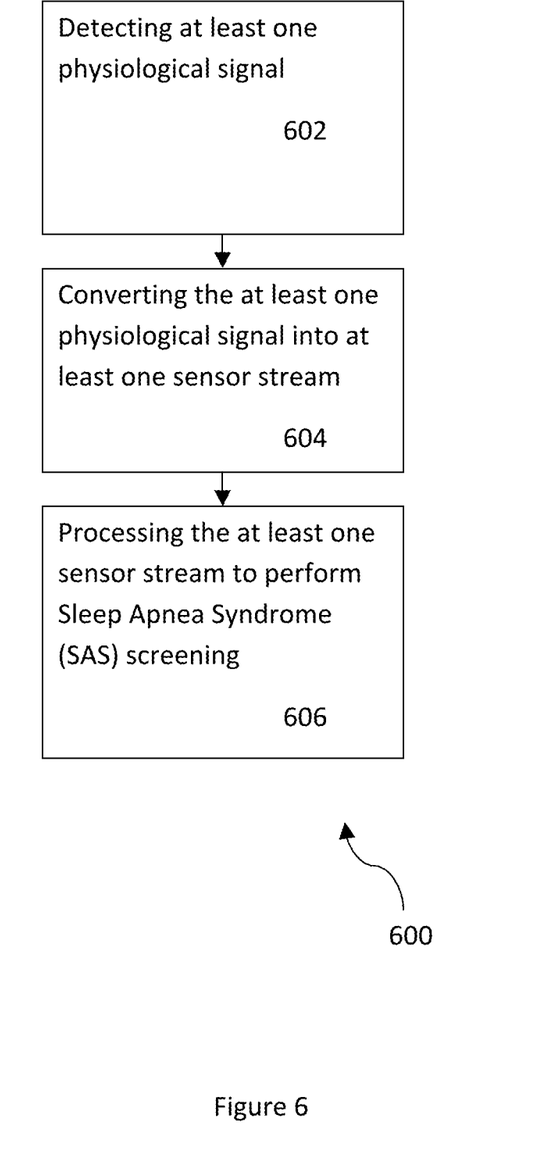
FIG. 6 illustrates a method for Sleep Apnea Syndrome (SAS) screening in accordance with an embodiment.

FIG. 6 illustrates a method 600 for Sleep Apnea Syndrome (SAS) screening in accordance with an embodiment. The method 600 comprises detecting at least one physiological signal, via step 602, converting the at least one physiological signal into at least one sensor stream, via step 604, and processing the at least one sensor stream to perform the SAS screening, via step 606.

In one embodiment, the detecting step is performed by a wearable device, the at least one physiological signal includes any of an ECG signal and an accelerometer signal, the converting step is performed by an electronic module of the wearable device, and the at least one sensor stream includes any of an RR interval, an amplitude of the QRS waveform (RWA), an area of the QRS waveform (RA), a MEMS derived respiration signal, a signal magnitude area (SMA) of an accelerometer signal, and posture angles.

In one embodiment, the processing step further comprises any of preprocessing the at least one sensor stream, performing feature extraction on the at least one preprocessed sensor stream to provide a feature vector, and performing machine learning optimization using the feature vector. In one embodiment, the processing step is performed by the wearable device and in another embodiment, an external device including but not limited to a sensor/relay/cloud processor, a smartphone device, and a cloud computing system performs the processing step.

In one embodiment, the preprocessing step further comprises any of eliminating wearable device off instances, removing trends, detecting and removing outliers, detecting and removing artifacts, normalization of ECG derived respiration signals, and normalization of MEMS derived respiration signals. In one embodiment, the performing feature extraction step utilizes any of time-domain analysis, statistical analysis, nonlinear analysis, frequency-domain analysis, and posture analysis to extract features from preprocessed sensor streams.

In one embodiment, the performing machine learning optimization step utilizes the feature vector and an optimized model to perform any of parameter optimization, feature selection, model optimization, and minimum misclassification error (MCE) determination. In one embodiment, the method 600 further comprises determining the feature vector using a combination of the feature extraction and patient information, and automatically performs SAS screening using overnight based signal analysis.

In one embodiment, the method 600 is performed using a wearable device that comprises a sensor to detect at least one physiological signal, a processor coupled to the sensor, and a memory device coupled to the processor, wherein the memory device includes an application that, when executed by the processor, causes the processor to perform the steps of the method 600.

System Overview:

In one embodiment, the wearable device is a Health-Patch™ device that is a disposable adhesive patch sensor that incorporates two surface electrodes with hydrogel on the bottom of the patch, a battery, and an electronic module with the embedded processor, micro-electro mechanical system (MEMS) tri-axial accelerometer and Bluetooth Low Energy (BLE) transceiver. One of ordinary skill in the art readily recognizes that the Health Patch™ device could have different hardware characteristics (e.g. a different type of Bluetooth or non-Bluetooth transceiver) and that would be within the spirit and scope of the present invention.

The wearable device facilitates continuous monitoring of single-lead bipolar ECG and actigraphy signals at a predetermined sampling rate (e.g. 125 and 62.5 Hz, respectively). The firmware algorithms on the electronic module process the raw ECG and acceleration signals and transmit a stream of processed physiological variables ("sensor streams") via the BLE wireless protocol as encrypted data to a relay including but not limited to a smartphone device where the live streams of data are stored and can be viewed and further processed/analyzed.

The wearable device utilizes a Sleep Apnea Syndrome screening algorithm (SAS screening algorithm) to screen for Sleep Apnea Syndrome (SAS). The SAS screening algorithm is located on any of the wearable device itself and on an external device including but not limited to a smartphone device and a cloud based server. SAS screening algorithm includes five major units: the sensor streams unit, the preprocessing unit, the feature extraction unit, the machine learning unit, and the display unit. The five major units are referred to the units 306-314 and of FIG. 3 and are described below in more detail.

Sensor Streams Unit:

In one embodiment, the sensor streams unit processes raw physiological data signals detected by the wearable device to provide sensor streams that are stored/recorded on any of memory of the wearable device and memory of an external device. The sensor streams are recorded in real-time during overnight sleep by a plurality of firmware algorithms implemented on the wearable device.

The sensor streams derived from detected ECG signals on a beat-to-beat basis include but are not limited to RR intervals, QRS wave amplitude (RWA) and QRS wave area (RA). A wavelet-based algorithm is used to detect the instantaneous time of the QRS wave peaks and identified as R peaks. The time intervals between successive R peaks are used to generate the RR intervals on a beat-to-beat basis. RWA and RA are measured as the range of ECG voltages and the absolute area under the ECG signal, respectively, within a predetermined window (e.g. 100 ms) centered at the R peak of each beat.

The sensor streams derived from detected tri-axial acceleration signals include but are not limited to MEMS-based respiration signals ($Resp_{MEMS}$), activity metrics called a signal magnitude area (SMA), and polar angles of posture. The body impedance value (in KΩ) is measured between the two electrodes of the wearable device. While ECG derived signals are recorded on a beat-to-beat basis, SMA, posture angles and body impedance are sampled every predetermined seconds (e.g. every 4 seconds) and the $Resp_{MEMS}$ is uniformly sampled at 4 Hz.

Preprocessing Unit:

In one embodiment, the preprocessing of sensor streams involves the identification of instances when the wearable device is "off" based on a predefined threshold of a body impedance value followed by the elimination of such off instances from all sensor streams of the sensor streams unit. Changes in posture during sleep such as supine, prone, left and right causes shifts in baseline of RWA and RA signals that introduce artifacts in the feature extraction performed by the feature extraction unit. Therefore, the beat-to-beat RWA and RA signals are filtered by a moving average filter with N beats (e.g. N=α×user's average Heart Rate (HR), where α is the number of minutes), which eliminates the very-low frequency trend. In one embodiment, α is 3 minutes which is arbitrarily chosen and does not affect the frequencies of interest.

If the relative change in successive RR intervals is greater than a predefined threshold including but not limited to 20% then the RR intervals are identified as artifacts/outliers and also eliminated. Artifacts/outliers of RWA, RA and $Resp_{MEMS}$ signals are identified as the values outside three standard deviations from the mean value of overnight signals. The RWA, RA, and $Resp_{MEMS}$ signals are normalized to unit variance with reference to a predetermined moving window (e.g. 3 minute moving window). After preprocessing, the sensor streams from an entire night of recording are fed/inputted into the feature extraction unit where features are derived and calculated.

Feature Extraction Unit:

In one embodiment, features are calculated by the feature extraction unit based on the overnight data analyses of heart rate variability (HRV), ECG and actigraphy derived respiratory signals, posture, and movements. The overnight data analyses consist of time-domain, frequency-domain, and nonlinear techniques that are applied on the preprocessed sensor streams to obtain the features and a feature vector.

The time-domain (TD) analysis includes but are not limited to the following features: median, standard deviation, coefficient of variation equal to the ratio of standard deviation to the mean, mean absolute deviation, kurtosis as a measure of peakedness of probability distribution, interquartile range as the difference between $75^{th}$ and $25^{th}$ quartiles, dispersion metric as the difference between $90^{th}$ and $10^{th}$ percentiles, and approximate entropy as a measure of complexity. The time-domain analysis is applied to the series of HRV, RWA, RA, $Resp_{MEMS}$ and SMA.

The beat-to-beat RR intervals are analyzed to obtain the following statistical and geometrical features (denoted as $STAT_{HRV}$) including but not limited to: mean, average of standard deviation of 5-minute normal beat (NN) intervals (ASDNN), standard deviation of average of 5-minute NN intervals (SDANN), root mean square of the successive differences between adjacent NN intervals (RMSSD), number of successive NN interval differences greater than 50 ms (NN50), percentage of NN50 with respect to the total number of NN intervals (pNN50), triangular index (TI8) equal to the ratio of total number of NN intervals to the height of the NN interval histogram with 8 ms bin widths, and triangular interpolation of NN intervals (TINN8) equal to the baseline width of the triangular approximation of the NN interval histogram with 8 ms bin widths.

The RR intervals are further analyzed using a nonlinear Poincare plot, which is a scatterplot of each (N-th) RR interval versus the next (N+1-st) RR interval. Poincare plot analysis derives the following features (denoted as $P_{HRV}$) including but not limited to: standard deviation of short-term variability (SD1) equal to the standard deviation of the projection of RR intervals on the line perpendicular to the identity line, standard deviation of long-term variability (SD2) equal to the standard deviation of the projection of RR intervals along the identity line, normalized SD1 and SD2 with reference to the average of RR intervals, overall variability (SDRR) calculated by $$SDRR = \frac{1}{\sqrt{2}}\sqrt{SD1^2 + SD2^2},$$

and the area of the fitted ellipse equal to s=π*SD1*SD2.

For the frequency-domain (FD) analysis, the beat-to-beat HRV, RWA and RA series are uniformly resampled to 4 Hz using spline interpolation. A power spectral density (PSD) estimate is obtained using Welch's averaged, modified periodogram method with 50% overlap and Hamming windows. The PSD is used to calculate the following frequency-domain features including but not limited to: total band power (0.003-0.4 Hz), very low frequency (VLF) band power (0.003-0.04 Hz), low frequency (LF) band power (0.04-0.15 Hz), high frequency (HF) band power (0.15-0.4 Hz), normalized VLF, LF and HF power with respect to the total band power, LF/HF ratio, spectral kurtosis, spectral entropy and peak-to-mean ratio. The frequency-domain features are extracted from the uniformly sampled series of HRV, RWA, RA, and $RESP_{MEMS}$.

In addition to the above features, the polar angles of posture derived from tri-axial accelerometer data are used to obtain the posture features (denoted as POS) including but not limited to: the percentage of time supine, the percentage of time prone, the percentage of time on the left, the percentage of time on the right, the percentage of time upright, the mean overnight posture, and the number of postures over the entire night. The patient information (PINFO) is also used as a feature set that included height, weight, age, neck circumference, gender, body mass index (BMI), STOP-BANG score, Epworth sleepiness scale score, and Berlin score.

All of the above features are combined to form the feature vector ($F_V$) (as given below) that is inputted to the machine learning unit:

$$F_V=[PINF0, TD_{HRV}, STAT_{HRV}, FD_{HRV}, PP_{HRV}, TD_{RWA},$$
$$FD_{RWA}, TD_{RA}, FD_{RA}, TD_{rMEMS}, FD_{rMEMS}, TD_{SMA}, POS].$$

Machine Learning Unit:

In one embodiment, the following three independent binary classifications are investigated by the machine learning unit: (i) control (AHI<5) vs. apnea (AHI>=5), (ii) control-to-mild apnea (AHI<15) vs. moderate-to-severe apnea (AHI>=15) and (iii) control-to-moderate apnea (AHI<30) vs. severe apnea (AHI>=30).

An independent supervised machine learning classifier is used for each of the three classifications. For each classification, a classifier model is optimized. The feature vector ($F_V$) is first used to optimize the model parameters of the classifier model. The optimization of model parameters begins with defining with an array of values. For each of parameter value, the feature vector is split into training and validation data sets according to leave-one-out cross validation (LOOCV). The training feature vector is scaled to have zero-mean and unit variance.

The binary classifier model is trained on the training feature vector and their respective reference class labels (such as $y_i \in \{-1,1\}$). The validation feature vector is also scaled according to the shift and scale factors obtained from the training feature vector. The trained classifier model and the scaled validation feature vector are used to predict the class of the validation feature vector. The class predictions are carried out for (l+1) LOOCV cycles, and the misclassification error (MCE) is calculated as compared to the reference class labels and stored in an array of same size of C. The MCE values are similarly obtained for all the other C values. The optimal C parameter is found to be the one that offers the least MCE.

After the optimization of model parameters, the feature selection process is carried out using sequential backward selection with LOOCV. This method starts considering all the features and sequentially removes one feature at each step that results in the least MCE, until any further removal increases the error drastically. Thus, the optimized model parameters and the feature set both help to obtain optimal classifier model that offer highest performance, improved generalization capabilities, reduced complexity and less computational load. The classification decision is obtained for a given subject and the binary target group using the optimized classifier model and the input feature vector.

Display Unit:

In one embodiment, based on the classification decision, the display unit (e.g. smartphone application screen) will display either a "RED" or a "GREEN" light on a toggle arrangement panel indicating the subject might belong to positive or negative category, respectively, according to the chosen binary classification problem and determination of the presence and severity of SAS. One of ordinary skill in the art readily recognizes that a variety of display mechanisms can be utilized by the display unit and that would be within the spirit and scope of the present invention.

As above described, a method and system in accordance with the present invention utilizes a wearable device and a sleep apnea screening algorithm to provide Sleep Apnea Syndrome (SAS) screening. By utilizing the wearable device to detect a plurality of physiological signals (e.g. ECG) utilizing a plurality of embedded sensors (e.g. any of an ECG sensor, a MEMS accelerometer, and derived sensors) and utilizing a processor (e.g. any of an embedded processor in the wearable device, an external relay/cloud processor such as a smartphone device, and a cloud computing system) to perform preprocessing, feature extraction, and machine learning predictive analytics, the method and system in accordance with the present invention automatically screens a patient for SAS and classifies the patient into various subject groupings including but not limited to control, mild apnea, moderate apnea, severe apnea, low-risk apnea, and high-risk apnea.

The method and system in accordance with the present invention utilize a sleep apnea screening algorithm that is designed to be very robust and immune to motion artifacts and data loss, if any. The algorithm is capable of providing reliable performance for sleep apnea screening with ECG and actigraphy sensors alone, without blood oxygen saturation measurements. The algorithm is optimized using larger datasets such as multi-night overnight data.

A method and system for Sleep Apnea Syndrome (SAS) screening has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or calculator-readable medium. The software application provides instructions that enable the processor to perform the functions described herein.

Furthermore, embodiments may take the form of a calculator program product accessible from a calculator-usable or calculator-readable medium providing program code for use by or in connection with a calculator or any instruction execution system. For the purposes of this description, a calculator-usable or calculator-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a calculator-readable medium include a semiconductor or solid state memory, magnetic tape, a removable calculator diskette, a random access memory (RAM), a read-only memory (ROM), a rigid magnetic disk, and an optical disk. Current examples of optical disks include DVD, compact disk-read-only memory (CD-ROM), and compact disk—read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for Sleep Apnea Syndrome (SAS) screening, the method comprising:
   detecting at least one physiological signal;
   converting the at least one physiological signal into at least one sensor stream;
   preprocessing the at least one sensor stream;
   determining a feature vector using a combination of feature extraction on the at least one sensor stream and patient information; and
   performing machine learning optimization using the feature vector to perform the SAS screening.

2. The method of claim 1, wherein the detecting step is performed by a wearable device, further wherein the at least one physiological signal includes any of an ECG signal and an accelerometer signal.

3. The method of claim 2, wherein the converting step is performed by an electronic module of the wearable device, further wherein the at least one sensor stream includes any of an RR interval, an amplitude of the QRS waveform (RWA), an area of the QRS waveform (RA), a MEMS derived respiration signal, a signal magnitude area (SMA) of an accelerometer signal, and a posture angle.

4. The method of claim 1, wherein the processing step is performed by any of a wearable device, an external device, a relay/cloud processor, a smartphone device, and a cloud computing system.

5. The method of claim 1, wherein the preprocessing step further comprises any of eliminating wearable device off instances, removing trends, detecting and removing outliers, detecting and removing artifacts, normalization of ECG derived respiration signals, and normalization of MEMS derived respiration signals.

6. The method of claim 1, wherein the performing feature extraction step utilizes any of time-domain analysis, statistical analysis, nonlinear analysis, frequency-domain analysis, and posture analysis to extract features from the at least one preprocessed sensor stream.

7. The method of claim 1, wherein the performing machine learning optimization step utilizes the feature vector and an optimized model to perform any of parameter optimization, feature selection, model optimization, and minimum misclassification error (MCE) determination.

8. The method of claim 1, further comprising:
   automatically screen SAS disorder using overnight based signal analysis that does not involve computation of apnea and hypopnea Index values.

9. A wearable device for Sleep Apnea Syndrome (SAS) screening, the wearable device comprising a sensor to detect at least one physiological signal, a processor coupled to the sensor, and a memory device coupled to the processor, wherein the memory device includes an application that, when executed by the processor, causes the processor to:
   convert the at least one physiological signal into at least one sensor stream;
   preprocess the at least one sensor stream;
   determine a feature vector using a combination of feature extraction on the at least one sensor stream and patient information; and
   perform machine learning optimization using the feature vector to perform the SAS screening.

10. The wearable device of claim 9, wherein the at least one physiological signal includes any of an ECG signal and an accelerometer signal.

11. The wearable device of claim 10, wherein the at least one sensor stream includes any of an RR interval, an amplitude of the QRS waveform (RWA), an area of the QRS waveform (RA), a MEMS derived respiration signal, a signal magnitude area (SMA) of an accelerometer signal, and a posture angle.

12. The wearable device of claim 9, wherein any of the preprocessing, feature extraction, and machine learning optimization is performed by a processor external to the wearable device, wherein the external processor includes any of an external device, a relay/cloud processor, a smartphone device, and a cloud computing system.

13. The wearable device of claim 9, wherein the preprocessing further comprises any of eliminating wearable device off instances, removing trends, detecting and removing outliers, detecting and removing artifacts, normalization of ECG derived respiration signals, and normalization of MEMS derived respiration signals.

14. The wearable device of claim 9, wherein the feature extraction utilizes any of time-domain analysis, statistical analysis, nonlinear analysis, frequency-domain analysis, and posture analysis to extract features from the at least one preprocessed sensor stream.

15. The wearable device of claim 9, wherein the machine learning optimization utilizes the feature vector and an optimized model to perform any of parameter optimization, feature selection, model optimization, and minimum classification error (MCE) determination.

16. The wearable device of claim 9, wherein the application, when executed by the processor, further causes the processor to:
   automatically screen SAS disorder using overnight based signal analysis that does not involve computation of apnea and hypopnea Index values.

* * * * *